US007885827B1

(12) United States Patent
Koneru (10) Patent No.: US 7,885,827 B1
(45) Date of Patent: *Feb. 8, 2011

(54) METHOD AND SYSTEM FOR DELIVERING SUBSTITUTE MEDICAL THERAPIES WITH RESTRICTED ACCESS

(75) Inventor: Phanesh Koneru, Ashburn, VA (US)

(73) Assignee: Exela Pharmsci, Inc., Ashburn, VA (US)

( * ) Notice: Subject to any disclaimer, the term of this patent is extended or adjusted under 35 U.S.C. 154(b) by 0 days.

This patent is subject to a terminal disclaimer.

(21) Appl. No.: 12/813,028

(22) Filed: Jun. 10, 2010

Related U.S. Application Data

(63) Continuation of application No. 11/427,762, filed on Jun. 29, 2006, now Pat. No. 7,765,110, which is a continuation of application No. 11/392,531, filed on Mar. 29, 2006, now abandoned.

(60) Provisional application No. 60/666,513, filed on Mar. 29, 2005, provisional application No. 60/689,913, filed on Jun. 13, 2005.

(51) Int. Cl.
*G06Q 10/00* (2006.01)
*G06Q 50/00* (2006.01)

(52) U.S. Cl. .......................................... 705/2
(58) Field of Classification Search ................ 705/2, 705/4
See application file for complete search history.

(56) References Cited

U.S. PATENT DOCUMENTS

| 5,737,539 | A | 4/1998 | Edelson et al. |
|---|---|---|---|
| 6,202,923 | B1 | 3/2001 | Boyer et al. |
| 6,260,761 | B1 | 7/2001 | Peoples, Jr. |
| 6,315,720 | B1 | 11/2001 | Williams et al. |
| 6,687,676 | B1 | 2/2004 | Denny |
| 6,711,460 | B1 | 3/2004 | Reese |
| 7,111,780 | B2 | 9/2006 | Broussard et al. |
| 2002/0029223 | A1 | 3/2002 | Rice et al. |

(Continued)

OTHER PUBLICATIONS

Isotretinoin Risk Management Information (iPLEDGE and SMART).

(Continued)

*Primary Examiner*—Gerald J. O'Connor
*Assistant Examiner*—John A Pauls
(74) *Attorney, Agent, or Firm*—Frommer Lawrence & Haug LLP; Brian J. Malkin (57) ABSTRACT

A system and methods are provided for delivering to a patient a substitute medical therapy with restricted distribution or access. One example is a medical therapy provider, such as a pharmacist, receiving a prescription for a medical therapy for a patient and describing these procedures and the substitute medical therapy to the patient. The patient and patient's prescribing physician will determine whether the proposed substitute medical therapy is desired and would be indicated for this patient, including obtaining data and informed consent from the patient. The method also provides a distributor or third party reviewer the prescription and certification from a qualified patient's physician, data and consent from a qualified patient, including an authorization for the substitute medical therapy and confirming the informed consent from a qualified patient by the distributor or a third party reviewer. From this data, the distributor or third party reviewer determines the qualified patient's eligibility for access to the medical therapy and, if the qualified patient is found eligible, delivers the medical therapy to the patient.

40 Claims, 4 Drawing Sheets

U.S. PATENT DOCUMENTS

| | | |
|---|---|---|
| 2003/0125986 A1 | 7/2003 | Collosi |
| 2004/0019567 A1 | 1/2004 | Herceg et al. |
| 2004/0019794 A1 | 1/2004 | Moradi et al. |
| 2004/0081669 A1 | 4/2004 | Greeven et al. |
| 2004/0148196 A1 | 7/2004 | Kalies |
| 2004/0153336 A1 | 8/2004 | Virdee et al. |
| 2004/0215369 A1 | 10/2004 | Rosenblum |
| 2005/0065645 A1 | 3/2005 | Liff et al. |
| 2005/0108053 A1 | 5/2005 | Jones, Jr. |

OTHER PUBLICATIONS

Thalomid® Risk Management Information (S.T.E.P.S.).
Clozaril® Risk Management Information (Clozaril National Registry (CNR)).
Xyrem® Risk Management Information (Physician Success Program).
Revlimid® Risk Management Information (Rev Asst).
Tracleer® Risk Management Information (Tracleer Access Program (T.A.P.).

METHOD AND SYSTEM FOR DELIVERING SUBSTITUTE MEDICAL THERAPIES WITH RESTRICTED ACCESS

CROSS-REFERENCE TO RELATED APPLICATIONS

This application is a continuation of U.S. application Ser. No. 11/427,762, filed Jun. 29, 2006 now U.S. Pat. No. 7,765,110, which is a continuation of U.S. application Ser. No. 11/392,531 filed Mar. 29, 2006 now abandoned, and claims the benefit of provisional applications 60/666,513 filed Mar. 29, 2005 and 60/689,913 filed Jun. 13, 2005, which are hereby incorporated by reference in their entirety herein.

1. FIELD OF INVENTION

The present invention relates generally to a system and method for delivering, to a patient, a substitute medical therapy with restricted distribution or access. More particularly, the present invention relates to a method, for delivering, to a patient, a substitute medical therapy while preventing access to the substitute medical therapy for individuals for whom the medical therapy would be contraindicated or otherwise restricted.

2. BACKGROUND

Typically, when a physician prescribes a prescription for a particular medical therapy, the physician may specify a particular brand name for the medical therapy, because the physician is familiar with this brand or, in some instances, the physician may not be aware that there is a substitute medical therapy available. These substitute medical therapies represent additional options for patients, which may provide enhanced benefits, and/or lower cost, depending on the patient's medical care coverage.

For example, a physician could specify a brand name for a therapeutic dosage of an active pharmaceutical ingredient (API), i.e., a "branded product", when there is a substitute generic pharmaceutical product, approved by a regulatory authority, such as the Food and Drug Administration (FDA), with the same API. In some instances, the generic pharmaceutical may be a direct substitute, i.e., therapeutically and pharmaceutically equivalent or "bioequivalent." In other instances, the product may contain the same API, at a similar dosage or with a different release profile or dosage form. In yet other instances, there may be substitute pharmaceutical products that treat the same medical condition for which the original branded product was prescribed.

Furthermore, the substitute medical therapy could be an alternative biological or medical device, or another medical therapy. For example, a physician could specify a particular brand of therapeutic proteins, when another brand would provide the patient with greater safety, effectiveness, or a substantial savings, based on the applicable medical insurance coverage for the prescribed medical therapy. Likewise, there could be a substitute medical device, e.g., syringes, or another medical therapy with a similar therapeutic use.

For substitute products with the same API, pharmacists are often able to offer patients an option to substitute medical therapies. For example, many state laws require pharmacists to substitute generic pharmaceuticals, when a generic pharmaceutical is available for a branded product, i.e., a medical therapy with a proprietary name. In other instances, pharmacists may offer a patient the option for a generic pharmaceutical, because it would save the patient money, based on the patient's medical insurance coverage. In yet other instances, a patient may be required for medical insurance coverage to substitute for the prescribed branded drug medical therapy with a similar therapeutic use but a different API, often because the substitute API has an available generic pharmaceutical. For example, an insurance company could require a patient to use a generic form of birth control pharmaceutical over a new, branded birth control pharmaceutical product.

In some cases, the physician may choose to prevent generic or other substitution by specifically requiring that the prescription may be dispensed or delivered only with the branded product. In other instances, direct substitution may not be possible, because there is no substitute product, or the product is provided with restricted access. In the latter case, a generic product may be available, but it may be available only under a different restricted access program.

FDA required, for example, the manufacturers of the initial generic products for Accutane® (generic: isotretinoin), to provide risk management programs that contained the "same essential elements" of the risk management program developed for the branded product. Because isotretinoin is a potent teratogen with potential to cause severe birth defects, both the branded and generic risk management programs were designed to help prevent fetal exposure to isotretinoin. The initial risk management programs for the generic isotretinoin were separately maintained and managed, but the prescriptions were delivered similarly at the pharmacy.

Conventional approaches for delivering a substitute medical therapy, such as a generic pharmaceutical, with restricted access or distribution have not always been successful. In some situations, moreover, the substitute medical therapy may even provide an alternative restricted access or distribution that achieves the same goals. For example, there is no generic substitute for the branded pharmaceutical Thalomid® (generic: thalidomide). The restricted access program for Thalomid® requires dispensing pharmacies to be "registered" and prescriptions to be "validated" in a computer readable medium that can only be accessed by "registered" pharmacies. Pharmacies that choose not to be "registered", for example, may not dispense Thalomid®, because they do not have access to the computer-generated validation code. As a result, generic manufacturers must develop alternative methods to deliver thalidomide to potential patients through an alternative distribution channel.

One example of a proposed invention for providing substitution of equivalent medical therapies related to U.S. Patent Application No. 2005/0065645, submitted by Liff, et al., entitled, "Method for Controlling a Drug Dispensing System." This relates to an automated pharmaceutical dispensing system to receive and dispense a prescription via an adapted cabinet, which involves providing the operator an opportunity to select a generic substitution product. The system updates label data to include the generic drug information, maintains an inventory and keeps track of the drugs that have been dispensed.

Another example where pharmaceuticals may be substituted concerns U.S. Pat. No. 6,260,761, issued, to Peoples, entitled, "System and Method for Accurately Dispensing Prescriptions in a Pharmacy." This relates to a device and method for converting product-specific identification numbers associated with bar code indicia on pharmaceutical products to an industry standard identification number. The process involves reading a bar code indicia, converting the indicia into an input string and standardizing the input string by means of adding or subtracting characters in accordance with rules based on the bar code length and input string. Pharmaceutical products of two different sources may be compared to determine if they contain the same drug as determined by the standard identification number. After receiving prescription information (bar code) that identifies a requested medical item, a substitution list is created that identifies at least one requested medical item and an equivalent item, and outputs the dispensing information for the selected medical item on the substitution list in response to substitution rules in a database.

Another example where pharmaceuticals may be substituted relates to U.S. Patent Application No. 2004/0215369, submitted by Rosenblum entitled, "Automatic Prescription Drug Dispenser." This relates to an automatic prescription drug dispenser, including a remote dispenser, a prescription entry system, and a communications network. The remote dispenser transmits and receives information from the communications network and dispenses prescription drugs to the patient. The prescription entry system transmits and receives information from the communications network and provides an input system for the prescriber to electronically enter individual prescriptions for each patient. The communications network coordinates communications between the prescriber, insurance carrier, and the remote dispenser. As part of the prescription writing process, the patient's insurance plan can be uploaded to the computer along with other patient information. Each drug viewed by the prescriber will usually indicate whether it is on the patient's insurer's formulary along with its approval status and whether the drug is in the remote dispenser. If the drug is not on the insurer's formulary, the prescriber may be prompted to a drug of the same therapeutic class that is covered on the patient's insurer's formulary. If the drug is not in the remote dispenser, the prescriber may determine from the patient whether the patient desires any of the products available from any of the remote dispensers, or, if not available, a printed traditional prescription that may be taken to a pharmacy of the patient's choice for dispensing.

Yet another example where pharmaceuticals may be substituted concerns U.S. Patent Application No. 2004/0153336, submitted by Virdee, et al entitled, "Prescription Creation and Adjudication Method." This relates to a computer-implemented method for creating a prescription for treatment of an injury or illness covered by a workers' compensation system, which facilitates on-line adjudication of workers' compensation claim. The patient name, employer name and type and quantity of medication prescribed are input. During prescription writing, a formulary text box can be used to provide an indication whether the prescribed medication is included in the patient's formulary by comparing the prescribed medication to a list of medications contained in a formulary database. The user can obtain further information on the drugs in the drug database or can identify alternative medications by selecting an alternative medication link. The selected drugs will appear in a currently selected medications list, where a prescription provider may then be selected to route the claim for on-line adjudication and to fill the prescription.

SUMMARY OF THE INVENTION

The present invention is directed toward a method and apparatus that delivers a substitute medical therapy to a patient with restricted distribution or access by a pharmacy or other medical therapy provider. The medical therapy and substitute medical therapy is typically provided with restricted distribution or access to prevent access for individuals for whom the medical therapy would be contraindicated or otherwise restricted. The delivery is accomplished by a medical therapy provider first identifying a substitute medical therapy and obtaining data regarding the restricted access for obtaining the substitute medical therapy.

Accordingly, one embodiment of the present invention relates to a method and apparatus for determining whether a patient desires access to the substitute medical therapy once the patient becomes aware of the substitute medical therapy with restricted access. If the patient requests the substitute medical therapy, the patient's prescribing physician determines whether the physician will certify that the patient qualifies for access to the substitute medical therapy. The physician certification includes an agreement to follow the requirements of the restricted access for the substitute medical therapy. The physician's determination may include obtaining additional patient data and informed consent for the substitute medical therapy. The patient's and prescriber's data is compared with the requirements for determining access to the medical therapy by a third party, for example, a distribution party.

Another embodiment of the present invention provides the embodiment described above and, further obtaining data regarding the procedure for delivering a substitute medical therapy.

A further embodiment of the present invention relates to the embodiment described above and, further, for each patient found eligible for access to the substitute medical therapy, distributing the substitute medical therapy.

Yet another embodiment of the present invention relates to the embodiment described above and, further, providing prescription data to the prescribing physician.

Another embodiment of the present invention relates to the embodiment described above, and further, confirming prescription data, including the prescription label and eligibility determination.

Yet another embodiment of the present invention relates to the embodiment described above, and, further, obtaining additional information from the patient to determine present or future qualification or eligibility for the substitute therapy or for quality control purposes.

BRIEF DESCRIPTION OF THE DRAWINGS

The invention will be understood more completely with reference to the following detailed description and Figures in which like numerals refer to like elements.

DETAILED DESCRIPTION

The present invention relates to a system and method for delivering a substitute medical therapy to a patient with restricted distribution or access. The method prevents access to the substitute medical therapy for individuals for whom the medical therapy would be contraindicated or otherwise restricted.

While it is possible to apply this invention to a variety of medical therapies, one embodiment of the present invention may be used to deliver a drug with the potential for serious adverse events to the patient or a developing fetus or with the potential for substance abuse or clinical dependence.

The present invention provides a solution for delivering a substitute medical therapy with restricted access or distribution that may not be delivered via the same restricted access or distribution process as the prescribed medical therapy. Because of the unique and sometimes complex problems associated with transferring a prescription from one restricted distribution or access program to another, conventional techniques have not provided a method that permits the medical therapy provider, e.g., a pharmacist, to substitute these medical therapies for a patient. The present invention provides a method that goes beyond merely identifying or providing as an option a substitute medical therapy or substituting it in an adjudication process to assist the physician with writing the prescription for medical therapies included in a patient's formulary.

The medical therapy substitution is performed based on the informed consent of the patient requesting the substitute medical therapy and following an independent review by a distribution party or third party reviewer for the substitute therapy to ensure that the substitution is proper. Such methods are needed to increase patient accessibility to substitute medical therapies that may be required by a patient's medical care coverage or provide less costly alternatives, including generic pharmaceuticals.

An embodiment of the invention is a method for delivering a generic version of the pharmaceutical Thalomid® (generic: thalidomide) under the generic product's restricted distribution or access program. A pharmacy, for example, could use this invention for substituting generic thalidomide after being presented with a prescription for Thalomid® by a patient. While the present invention provides a delivery method for substituting the teratogenic drug thalidomide, the invention also may be employed for distributing any medical therapy that involves a restricted distribution or access program, such as, for example, thalidomide, lenalidomide, isotretinoin, bostentan, alosetron, dofetilide, drugs with a high abuse potential or chemical dependence, which may be regulated in part by the U.S. Drug Enforcement Agency (DEA), such as oxycodone, marijuana, or cannabis, or any medical therapy that requires ongoing diagnostic testing for continued therapy, such as clozapine.

According to the present invention, a medical therapy provider, such as a pharmacist, would first receive a prescription from a patient for a medical therapy. When the medical therapy provider (generally referred to herein as "provider") first receives this prescription, the provider follows its customary practice for delivering the prescribed medical therapy. Such practices typically include checking the provider's inventory to determine whether the prescribed medical therapy may be immediately delivered or must be ordered.

A provider may become aware of a substitute medical therapy for the one prescribed. This awareness may be based on the provider's own knowledge, the provider's inventory database, or any other indicating means. In some instances, the substitute medical therapy could be a generic pharmaceutical version of the branded product, typically approved under Section 505(j) of the Federal Food, Drug and Cosmetic Act (FDCA) as a bioequivalent drug, i.e., therapeutically and pharmaceutically equivalent (same API), to the branded product. In other instances the substitute medical therapy could be approved under 505(b)(2) of the FDCA, which generally contains the same API as the branded product (or same therapeutic use) but is not bioequivalent or required additional clinical trials for approval by the FDA. In yet other circumstances, the substitute medical therapy could be an alternative therapy in the same class of therapeutics, e.g., birth control pharmaceuticals, a biologic, e.g., a product derived from live biological material, a medical device, or another substitute medical therapy for the written prescription.

Unlike other substitute medical therapies, such as most generic pharmaceuticals that do not have restricted distribution or access, the provider would not be able to merely provide the substitute medical therapy to the patient with the prescription. Instead, the provider would need to be in possession of or obtain information about the restricted distribution program associated with the substitute medical therapy and the requirements for delivering the substitute medical therapy to a patient. In some instances, the substitute medical therapy would be provided under the same restricted distribution program but would not have the same manufacturer or distributor as the branded product. In other instances, the substitute medical therapy would be provided under a similar, but alternative, restricted access program. In most cases, the alternative restricted access program is designed to accomplish the same goals as the branded restricted distribution program. For example, the generic isotretinoin programs sought to educate patients about isotretinoin's teratogenic effects and why isotretinoin may not be taken by pregnant females as part of the required essential elements for all isotretinoin restricted access programs.

After becoming aware of the substitute medical therapy with restricted access, the provider may need to obtain additional information about the substitute medical therapy's restricted distribution program to determine whether it may be beneficial for the patient, e.g., it may cost less under the patient's present medical coverage or it may offer other enhanced benefits for this patient. Enhanced benefits may include, for example, a different route of administration or dosing schedule that may be preferred by a particular patient. The provider typically then explains to the patient the substitute medical therapy, its risks and benefits, and the requirements for access to the substitute medical therapy.

If the patient determines that the potential benefit of the substitute medical therapy outweighs the risks and requirements for the substitute medical therapy, the provider obtains the required consent for delivering the substitute medical therapy. The informed consent may include an authorization to release the medical records from the prescribing physician of the patient with a qualifying prescription to deliver the substitute medical therapy. The consent may acknowledge receipt of data about the substitute medical therapy's adverse effects or potential for adverse effects, as well as the proper standard of care for delivering and administering the substitute medical therapy. Typically, the informed consent may also include a request that the substitute medical therapy be delivered based on the original prescription. The patient, or patient's prescribing physician, may be required to agree to certain requirements associated with the restricted access for the substitute medical therapy, for example, a certification to follow all of the listed requirements for access to the substitute medical therapy, and, in some cases, may write a new prescription for the substitute therapy. In addition, the patient may undergo additional diagnostic testing for access to the substitute medical therapy.

The provider typically provides the patient's informed consent and prescription to a distribution party or third party reviewer, but may also provide this information to the patient's prescriber. This information could be forwarded, for example, to a distributor, e.g., a wholesale distributor, manufacturer, or a third party that assumes the role of a distributor. The instructions for this process would typically be included in the data obtained by the provider for delivering the substitute medical therapy.

The distributor may review the prescription, informed consent, authorization to release the patient's medical records from the patient's prescribing physician, and request for patient with a qualifying prescription to be provided access to the substitute medical therapy and could determine whether the patient met the requirements and is, therefore, eligible for access to the substitute medical therapy. Prior to making a determination, the distributor could obtain certain certification data and any required diagnostic tests, typically from the patient's prescribing physician.

The certification data would include conclusions from the patient's prescribing physician that the patient is a qualified patient for the substitute medical therapy based on the qualifying prescription and other data. The certification would also include the prescribing physician's representations that he/she will follow the requirements to access the substitute medical therapy. For example, the distributor could determine that the required data were complete and accurate and verify certain information where appropriate. The distributor could also register the patient and physician and store this data in a computer readable medium, for record keeping purposes and to facilitate other data collection.

Furthermore, following an initial review of the data, the distributor could consult with the patient or the patient's physician. The consultation may be voice-recorded, to aid in the determination whether the qualified patient with a prescription for a different specific medical therapy should be provided access to the substitute medical therapy. For example, this distributor could verify medical coverage, a physician's medical license or Drug Enforcement Administration (DEA) registration number, that the physician has examined this patient, or a patient's understanding of the data associated with the substitute medical therapy and its restricted access.

When this distributor determines that the patient is eligible for access to the substitute medical therapy, the distributor could deliver, as appropriate, the substitute medical therapy to the patient or designated delivery agent for the patient. The distributor may designate a pharmacy, manufacturer, a wholesale distributor, or a third party to deliver the substitute medical therapy. In many cases, the provider may request to initially receive the substitute medical therapy for the patient, because of the provider's relationship with the patient. The distributor may use, for example, a conventional, confirmed delivery mechanism for the substitute medical therapy that obtains a signature upon delivery. This may include, for example, a carrier such as Federal Express, United Parcel Service, or DHL.

The substitute medical therapy generally comprises the substitute medical therapy, along with its attendant labeling, which typically has been approved for use by the FDA. Such labeling may include a patient guide, prescribing information, or audiovisual materials, for example, to supplement the patient guide and prescribing information.

Alternatively, if it is not possible for the eligible patient to sign for the delivery, the distributor could send the substitute medical therapy, for example, to the patient's physician or pharmacist, provided the substitute medical therapy is delivered according to applicable laws or labeling requirements for the medical therapy.

Additionally, the confirmed delivery of the substitute medical therapy to the eligible patient may be recorded in a database available in a computer readable medium, along with other prescription relevant data. For example, the distributor could record data in a central database including the patient's name, prescription delivered, a copy of the prescription labeling for this patient, and data concerning the distributor's determination that the patient should be provided access to the substitute medial therapy in this instance. The distributor's determination may include a voice recording of the informed consent from the qualified patient.

Alternatively, a confirmation letter or a copy of the prescription or other prescription relevant data may be provided to the eligible patient's physician to aid in determining the patient's potential for future medical therapy.

Following a distribution of the substitute medical therapy, the distributor may obtain additional data from the eligible patient or the eligible patient's physician to assess the patient's eligibility to obtain the substitute medical therapy in a subsequent prescription, for quality control, or as required by a regulatory authority that monitors the distribution of the restricted access substitute medical therapy.

Figure 1:
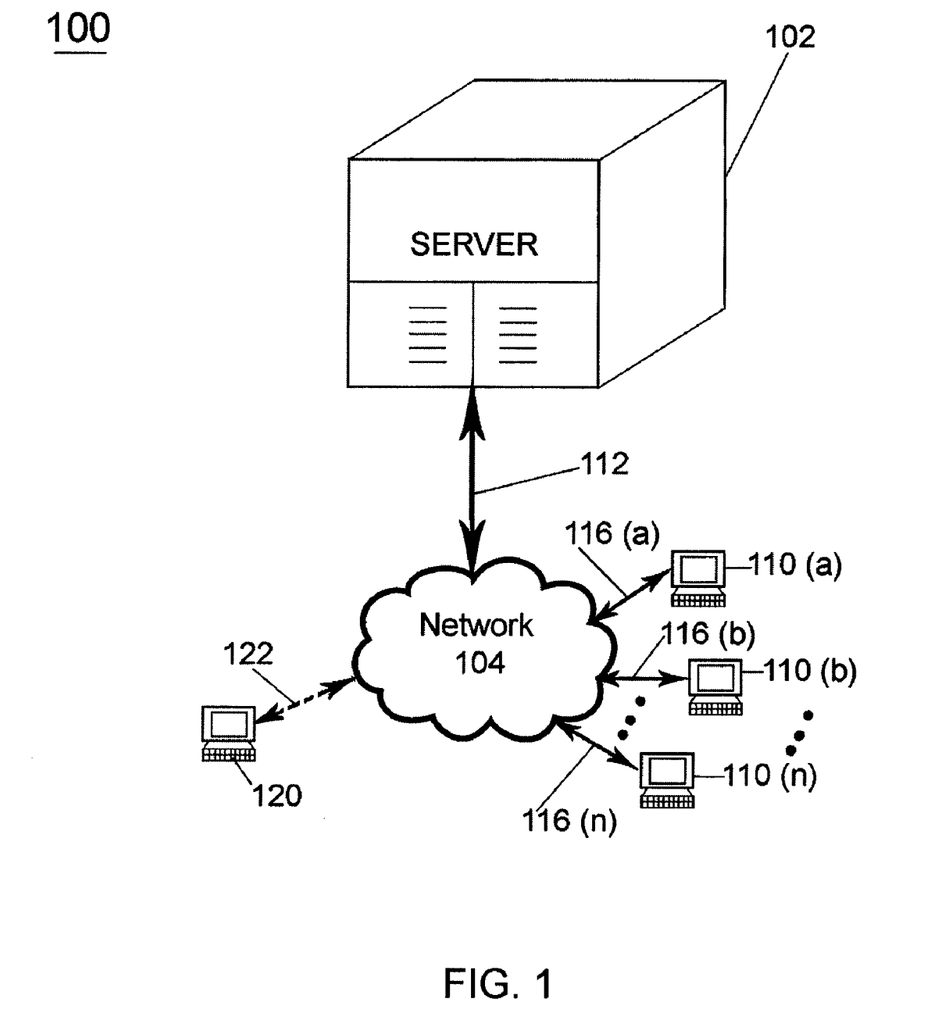
FIG. 1 shows a network environment adapted to support the proposed invention.

This invention may be implemented using one or more processing devices. The processing devices may be coupled such that portions of the processing and/or data manipulation may be performed at one or more processing devices and shared or transmitted between a plurality of processing devices. Thus, an example of the invention is described in a network environment. Specifically, FIG. 1 shows a network environment 100 adapted to support the present invention. The exemplary environment 100 includes a network 104, a server 102, a plurality of communication appliances, or user locations, or subscriber devices, or client terminals, 110(a)...(n) (where "n" is any suitable number) (collectively referred to herein as, client terminals 110) and the remote client terminals, represented by terminal 120.

The network 104 is, for example, any combination of linked computers, or processing devices, adapted to transfer and process data. The network 104 may be private Internet Protocol (IP) networks, as well as public IP networks, such as the Internet that can utilize World Wide Web (www) browsing functionality.

Server 102 is operatively connected to network 104, via bi-directional communication channel, or interconnector, 112, which may be for example a serial bus such as IEEE 1394, or other wire or wireless transmission medium. An example of a wireless transmission includes wireless application protocol (WAP). The terms "operatively connected" and "operatively coupled", as used herein, mean that the elements so connected or coupled are adapted to transmit and/or receive data, or otherwise communicate. The transmission, reception or communication is between the particular elements, and may or may not include other intermediary elements. This connection/coupling may or may not involve additional transmission media, or components, and may be within a single module or device or between the remote modules or devices.

The server 102 is adapted to transmit data to, and receive data from, client terminals 110 and 120, via the network 104. Server 102 is described in more detail with reference to FIG. 2, herein.

Client terminals 110 and 120 are typically computers, or other processing devices such as a desktop computer, laptop computer, personal digital assistant (PDA), wireless handheld device, and the like. They may be capable of processing and storing data themselves or merely capable of accessing processed and stored data from another location (i.e., both thin and fat terminals). These client terminals 110, 120 are operatively connected to network 104, via bi-directional communication channels 116, 122, respectively, which may be for example a serial bus such as IEEE 1394, or other wire or wireless transmission medium. Client terminals 110, 120 are described in more detail in relation to FIG. 3.

The server 102 and client terminals 110, 120 typically utilize a network service provider, such as an Internet Service Provider (ISP) or Application Service Provider (ASP) (ISP and ASP are not shown) to access resources of the network 104.

Figure 2:
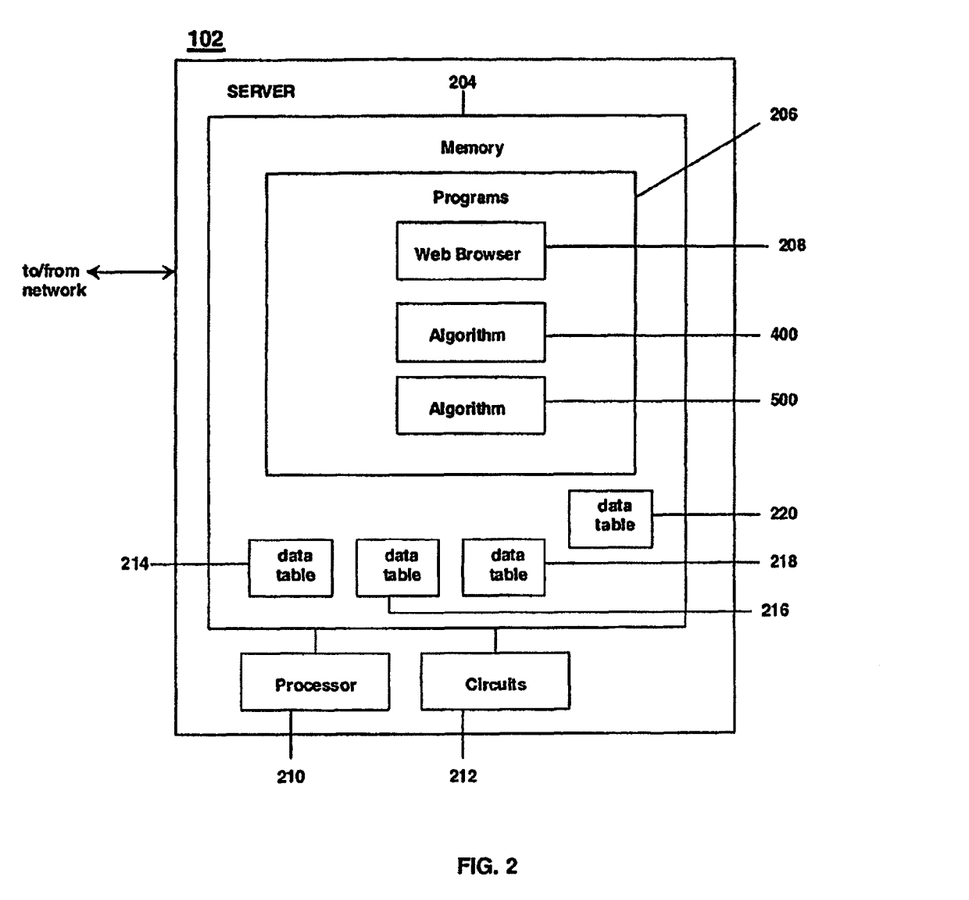
FIG. 2 illustrates a processing apparatus adapted to store and process data related to the present invention.

FIG. 2 illustrates that server 102, which is adapted to store and process data related to the present invention, is operatively connected to the network (shown as 104 in FIG. 1), via interconnector 112. Server 102 includes a memory 204, processor 210 and circuits 212. The server 102 may be operated by a distributor, such as a drug manufacturer or pharmacist, or other medical therapy distributing entity.

Memory 204 stores programs 206, which include, for example, a web browser 208, algorithm 400, as well as typical operating system programs (not shown), input/output programs (not shown), and other programs that facilitate operation of server 102. Web browser 208 is for example an Internet browser program such as Internet Explorer®. Algorithm 400 is a series of steps for manipulating selected data, which is typically stored on a computer-readable memory and executed by a processor. The process of the present invention typically generates a record of a delivered substitute medical therapy to a patient in accordance with a physician's prescription and requirements for restricted access. These functions may be implemented or facilitated by using software or other program code to sort the data and generate the representation. The algorithm 400 is discussed in more detail in relation to FIG. 4.

Memory 204 also stores data tables 214, 216, 218, and 220. These data tables are databases or memory locations adapted to store related data, which can be retrieved, processed, updated, modified or otherwise manipulated.

For example, data table 214 may be adapted to store prescription data related to a first patient; data table 216 may be adapted to store prescription data related to a second patient; and data table 218 may be adapted to store prescription data related to a third patient. Data table 220 may be adapted to store a subset of data collected from each patient. A patient's prescription data could include, for example, the patient's social security number, address, prescribing physician, and diagnostic test results. This data is typically obtained in relation to the physician's determination that a particular substitute medical therapy would be indicated or could be beneficial for a patient.

Processor 210, which is operatively connected to memory 204, is used to process and manipulate the data retrieved and stored by server 102 or from another device coupled to system 100. The processor 210 is typically a microprocessor with sufficient speed and processing capacity to adequately perform the desired data manipulations of server 102. Circuits 212 are operatively connected to processor 210 and typically include, for example, Integrated Circuits (ICs), ASICs (application specific ICs) power supplies, clock circuits, cache memory and the like, as well as other circuit components that assist in executing the software routines stored in the memory 204 and that facilitate the operation of processor 210.

Figure 3:
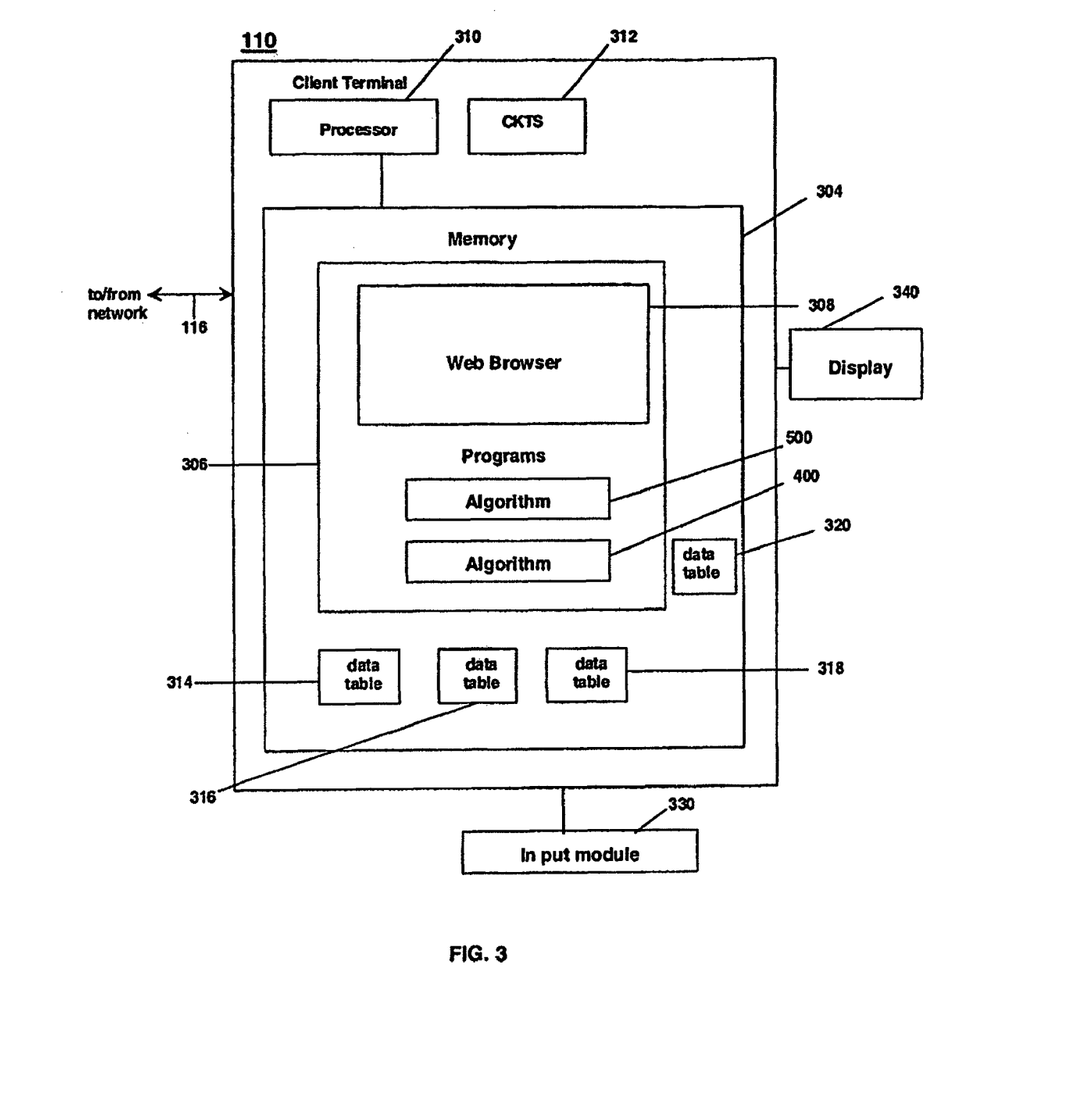
FIG. 3 illustrates a communication appliance shown in FIG. 1.

FIG. 3 illustrates subscriber terminal, also referred to herein as a client terminal, user terminal, or communication appliance 110. Terminal 110 is typically a desktop computer, laptop computer, PDA (personal digital assistant), wireless handheld device, mobile phone or other device capable of interfacing with a network, such as an IP network. Terminal 110 includes processor 310, support circuitry 312, memory 304, input module 330 and display module 340. Bi-directional interconnection medium 116 operatively connects the terminal 110 to the network (shown as element 104 in FIG. 1). The user terminal is typically located at the user location. The user may be, for example, a prescribing physician.

Processor 310, which is operatively connected to memory 304, is used to process and manipulate the data retrieved and stored by terminal 110. The processor 310 is typically a microprocessor with sufficient speed and processing capacity. The processor 310 is operatively connected to circuitry 312. Circuitry 312 typically includes, for example, Integrated Circuits (ICs), ASICs (application specific ICs) power supplies, clock circuits, cache memory and the like, as well as other circuit components that assist in executing the software routines stored in the memory 304 and that facilitate the operation of processor 310.

Memory 304 stores programs 306, which include, for example, a web browser 308, algorithm 400 as well as typical operating system programs (not shown), input/output programs (not shown), and other programs that facilitate operation of terminal 110. Web browser 308 is for example an Internet browser program such as Internet Explorer®. Algorithm 400 is a series of steps, typically executed by a processor such as, for example, processor 310, to manipulate selected data from the client terminal. Algorithm 400 is discussed in more detail in relation to FIG. 4.

Memory 304 also stores data tables 314, 316, 318, and 320. These data tables are databases or memory locations adapted to store related data, which can be retrieved, processed, updated, modified or otherwise manipulated.

Data table 314 is adapted to store prescription data related to a first patient; data table 316 adapted to store prescription data related to a second patient; and data table 318 is adapted to store prescription data related to a third patient. Data table 320 is adapted to store a subset of the data collected for each patient. A patient's prescription data could include, for example, the patient's social security number, address, age, gender, allergies, concurrent medical therapies, any disorders or disabilities such as diabetes, hypertension, etc., name of the prescribing physician, diagnostic test results, and medical therapy provider. This data is typically obtained in relation to the physician's determination that a particular substitute medical therapy would be indicated or could be beneficial for a patient.

Input module 330 is, for example, a keyboard, track ball, mouse, touch pad, menu having soft-keys, or any combination of such elements, or other input facility adapted to provide input to terminal 110. The physician can use these input facilities to input patient information into terminal 110.

Display module 340 is, for example, a monitor, LCD (liquid crystal display) display, GUI (graphical user interface) or other interface facility that is adapted to provide or display information to a user. Other display modules could include a printer or other output module.

Generally, the present invention is achieved in several steps, the order of which may vary for a particular product. A general discussion of several embodiments of the invention are discussed below, with more specific embodiments discussed in relation to FIG. 4.

Figure 4:
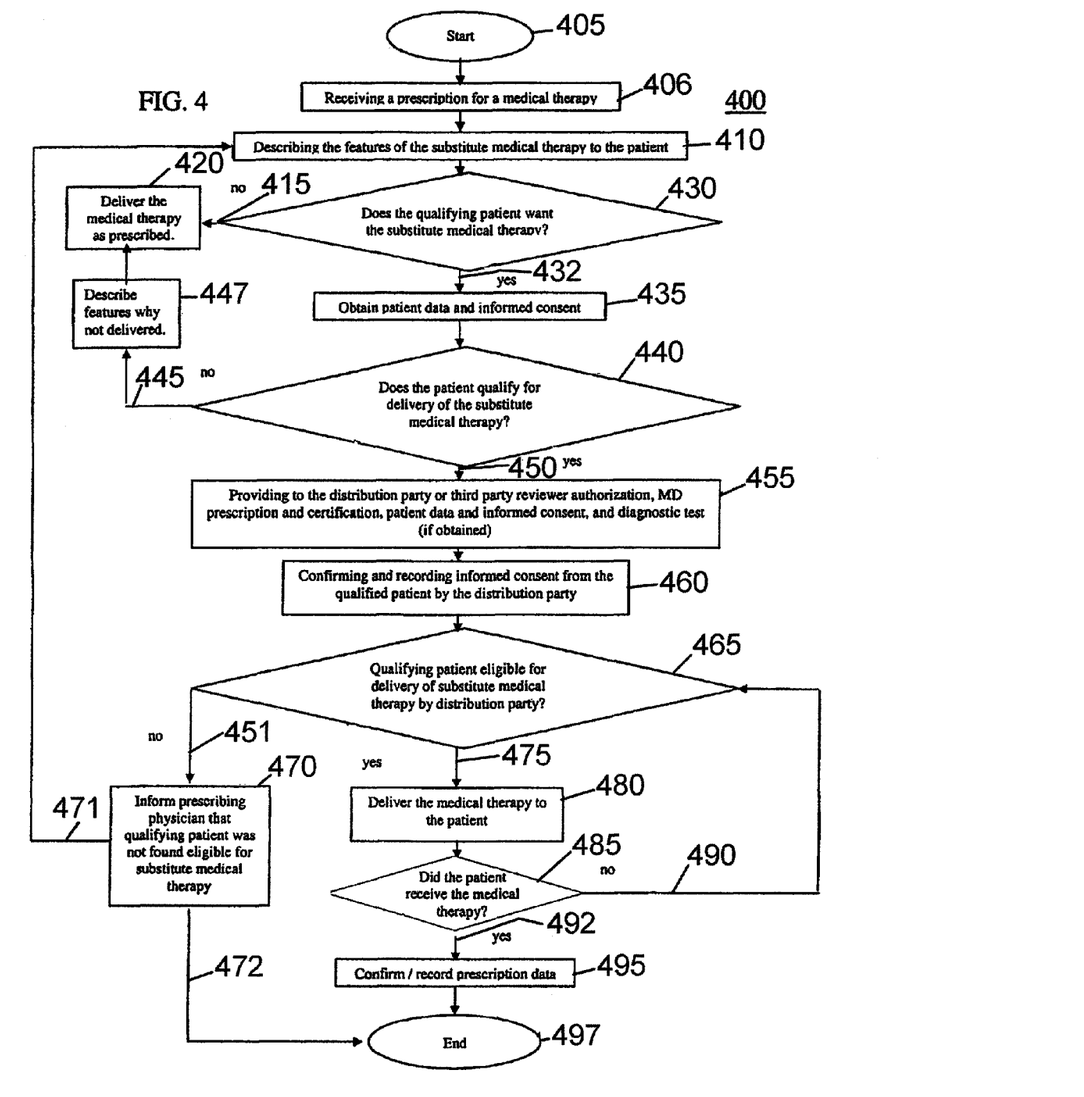
FIG. 4 is a flowchart of one embodiment of the present invention.

As shown in FIG. 4, algorithm 400 is a series of steps, some or all of the steps may be stored on a computer-readable medium that may be executed at a server, client terminal, or other processing device to implement the present invention. Step 405 begins execution of the algorithm. Step 406 shows that the medical provider receives a prescription for a medical therapy. For example, a medical therapy provider may receive a prescription by telephone or by a facsimile or by electronic means, such as an electronic mail (e-mail) message. The medical therapy provider may also receive a prescription directly from a patient or a patient's representative in person or by mail. Similarly, the distributor may receive a request from a physician or a pharmacist by telephone, or by facsimile, or by electronic means such as an electronic mail message, and in some cases, by mail or hand delivery.

Step 410 shows the requirement to describe the features of a substitute medical therapy to the patient to obtain access to the substitute medical therapy. The features of the substitute medical therapy may be described by the medical therapy provider or another health care professional, primarily based on the approved labeling for the medical therapy. These features could include, for example, data regarding the risks and benefits associated with the medical therapy and the restricted access. These features may also include the specific requirements for obtaining a certification from the patient's prescribing physician, as well as the additional requirements for eligibility that are reviewed and assessed by the distributor. One of additional requirements could include, for example, diagnostic tests administered to a potential patient. In the case of the teratogenic drug thalidomide, diagnostic tests may include a pregnancy test, if the potential patient is a fertile female.

In some cases, a medical therapy provider may need to obtain data regarding the procedures for delivering the substitute medical therapy to the patient with the prescription. Data may include the procedures or the cost for obtaining the substitute medical therapy, including its associated restricted distribution program. Data may also include, for example, certain relevant risk assessment documents that may be used by healthcare personnel, e.g., physician, physician's assistant, nurse, nurse practitioner, pharmacist, or distributor to assess whether the patient should be prescribed the substitute medical therapy, taking into account the risk profile of the drug and the patient's condition. For example, if the substitute medical therapy is a teratogen, such as thalidomide, the relevant risk may be the potential to become pregnant, if the patient is a fertile female, or the potential to impregnate a female, if the patient is a fertile male. If the substitute medical therapy is bosentan, as another example, the relevant risks may be the potential for pregnancy or impregnating a female and hepatotoxicity. In these cases, the relevant risk assessment documents may include a patient's recent pregnancy test results, menstrual cycle history, or a questionnaire with answers to a patient's sexual history, ability, and willingness to use pregnancy prevention measures, such as condoms or oral contraceptives. Relevant risk assessment documents for hepatotoxicity, as another example, may include liver function test results and a questionnaire with answers about a patient's alcohol consumption and other dietary habits.

Step 430 determines whether the patient wants the substitute medical therapy. The patient's decision is based on the information provided in step 410, and may include any additional diagnostic tests that may be required for the patient to determine whether the patient would be eligible for the substitute medical therapy. In the case of thalidomide, for example, if the patient is a fertile female, the patient may need to obtain an additional pregnancy test, if the prior pregnancy test were outdated for determining eligibility to initiate the substitute medical therapy. The patient's decision also may be motivated by his medical insurance coverage for the substitute medical therapy. For example, if the substitute medical therapy is a generic pharmaceutical, the generic pharmaceutical may cost the patient substantially less than the branded product. The patient's decision further may be motivated by the patient's perception of the benefits of the substitute medical therapy over the medical therapy for which he was originally prescribed. For example, a substitute medical therapy may offer a better dosing schedule or delivery means. If the answer to step 430 is "yes", line 432 leads to step 435. If the answer to step 430 is "no", line 415 leads to step 420.

Step 420 delivers the original medical therapy as prescribed to the patient. In this situation, the patient has determined that the substitute medical therapy would not be in the patient's best interest at this time. As a result, there is no need for the further processing steps in this invention, and the algorithm ends with step 497.

Step 435 obtains the required patient data and informed consent for receiving the substitute medical therapy. The required data could include the patient's social security number, home address, and other identifying information, medical history, or other information as required, such as a diagnostic test. In most instances, this data has already been obtained by the patient's prescribing physician. The patient's informed consent typically includes an authorization to release the patient's medical records from the patient's prescribing physician for the purpose of delivering the substitute medical therapy. The relevant data previously obtained from prescribing physician, therefore, may be used for the purpose of determining the patient's eligibility for the substitute medical therapy. The informed consent will typically include representations by the patient that the patient will follow the requirements for access to the substitute medical therapy. For instance, with thalidomide, a patient could agree to use one or more forms of birth control to prevent a pregnancy while taking the drug.

Step 440 determines whether the patient's prescribing physician agrees that the substitute medical therapy would be appropriate for the patient based on the physician's prior prescription for medical therapy and any new patient data and informed consent. The prescribing physician's decision is likely to include considerations for ease of transferring to the substitute restricted access program and familiarity with the substitute medical therapy and its restricted access. If the physician determines that the patient should be prescribed the substitute medical therapy under its conditions, typically, the physician must also certify that the patient is qualifying for a prescription and that the physician will monitor and follow the requirements associated with the restricted distribution of the substitute medical therapy. In some instances, the physician's prescription alone may be sufficient to satisfy this certification requirement, depending on the specific medical therapy involved. If the answer to step 440 is "no", line 445 leads to step 447. If the answer to step 440 is "yes", line 450 leads to step 455.

If the physician determines that the patient does not qualify for delivery of the substitute medical therapy, line 445 leads to step 447, where the physician would describe the features of the substitute medical therapy and indicate why the physician determined that the patient would not qualify to have the substitute medical therapy delivered at this time. In some instances, a patient could be qualified for the substitute medical therapy at a future date. For example, in the case of thalidomide, if a diagnostic test indicated that a patient were a pregnant female, the patient's physician could prescribe thalidomide in the future after the patient were no longer pregnant. As another example, a patient that provided a deficient informed consent, e.g., the patient did not agree to follow one or more of the requirements of the restricted distribution program for the substitute medical therapy, could in the future agree to those deficient requirements and become qualifying for the substitute medical therapy. Step 447 then leads to step 420.

Step 455 provides to the distributor certain preliminary information for the distributor or a third party reviewer to consider whether the patient with a prescription would be eligible for receiving the substitute medical therapy. In some instances, this information could be provided by the patient's physician, based on the patient's authorization to release medical records in its informed consent. Some of this information, however, may be provided by the medical therapy provider, e.g., the patient's authorization to release the patient's medical records to deliver the substitute medical therapy. The data may be received from a user terminal, web page, network device or other source of image data or sample data, and is typically transmitted over a network or other transmission medium. For example, data would be typically obtained via facsimile from a doctor's office and sent to the distribution party. The data would include the physician's prescription and certification (where applicable) and the patient's data, including any required diagnostic tests, and patient's authorization and informed consent. Some of this data may differ, depending on the particular patient. For example with thalidomide, data associated with a fertile female patient would include a negative pregnancy test (negative, because if it were positive, the potential patient's physician would not have found the patient qualifying for a prescription), whereas data associated with a fertile male patient would not include a negative pregnancy test.

The distribution party includes, in some aspects, the manufacturer that actually makes the substitute medical therapy and its authorized distributors and marketers and their representatives. Making a substitute medical therapy available for delivery to a patient with a qualifying prescription means performing some or all aspects of putting an FDA approved substitute medical therapy on the market. For example, for a pharmaceutical such activities may comprise making the drug substance (API), making the drug product (formulation), testing the drug product for its stability and bioequivalency/clinical equivalency, preparing labeling materials, filing for approval with the FDA, preparing commercial quantities of the drug product, labeling materials in anticipation of approval by the FDA, and distributing the drug product in interstate commerce to distributors, pharmacies, physicians, and patients.

Data may be provided in a variety of ways. For example, a pharmacist, upon receipt of a prescription for a pharmaceutical product with a restricted distribution program, may provide the prescription via facsimile or by electronic means, e.g., using commercial software to scan the prescription into an electronic document to be sent by an electronic mail message, to the distributor. In some aspects, the pharmacist may send the prescription (either transcribed, or original or a copy) to the distributor by courier or by mail or by hand delivery.

In step 460, the distributor confirms the informed consent provided by the patient. For later verification purposes or quality control, the distributor may choose to voice-record this conversation. Depending on the requirements of the restricted distribution program, this step may also involve describing and/or explaining the features of the substitute medical therapy or restricted access program to the patient. For example with thalidomide, this confirmation step could include verifying that the patient has been provided with and understands all of the necessary information to provide informed consent, i.e., risks and benefits of thalidomide, including its teratogenic effects, viewing or reading any instructional materials such as videotapes or product labeling brochures, and the requirements applicable to this qualifying patient for becoming eligible to receive thalidomide from the distributor. In other instances, the distributor may gather additional information to confirm the qualified patient's informed consent, which may then be used for the distributor to determine eligibility for delivery of the substitute medical therapy to this patient. For example, the distributor may gather additional information concerning the qualified patient's concomitant medication use or medical history, or willingness to comply with the requirements for delivery of the restricted access substitute medical therapy.

Step 465 determines whether the qualified patient is eligible for delivery of the restricted access substitute medical therapy by the distributor. At this stage of the process, at a minimum the distributor has reviewed the documents provided in step 455 and has confirmed or listened to the voice-recording of the patient's informed consent in step 460. The distributor may require additional information at this stage if, for example, the patient's informed consent indicates that additional information should be obtained from the patient's physician. The distributor may also routinely obtain certain information, such as calling the qualified patient's medical insurance provider to verify treatment for certain disease conditions or medical coverage for the medical therapy. This step includes evaluating the appropriateness of a prescription for a particular patient.

Evaluating the appropriateness of a prescription includes the determination made by the distributor, such as the manufacturer of the substitute medical therapy, upon receipt of relevant risk-assessment documents from the prescribing physician. The manufacturer may have physicians or pharmacists or nurses or other health care personnel evaluate the documents for appropriateness of the prescription. For example, if the drug is a teratogen, the prescription would be contraindicated if the patient is pregnant, and thus the prescription would be inappropriate. Similarly, upon reviewing the documents and upon consultation with the patient, the distributor may conclude that the patient may not be willing or able to avoid pregnancy while on the medication, if the prescription were to be dispensed. Prescription would be inappropriate in this case as well and the manufacturer may opt to deny the drug product or delay the delivery to a future date.

After the distributor makes its decision, if the answer to step 465 is "no", line 451 leads to step 470. If the answer to step 465 is "yes", line 475 leads to step 480.

Step 470 shows that the distributor will then inform the prescribing physician that the qualifying patient was not found eligible for the substitute medical therapy. In some instances, line 471 shows the distributor or pharmacist will then describe the features of a substitute medical therapy in step 410 and proceed as before. A qualified patient could become eligible for delivery by the distributor at a future date. For example, in the case of thalidomide, if the distributor were unable to reach the qualified patient within a certain time period, certain diagnostic tests related to requirements could become outdated. In the case of thalidomide, a diagnostic test for a qualified female patient would be a negative pregnancy test. If the negative pregnancy test were conducted outside the prescribed time period, as indicated in the restricted distribution program, the qualified patient could become eligible for delivery by submitting a complying pregnancy test to the distributor. As another example, a patient that provided a valid written informed consent but then was unable to confirm the informed consent during the initial discussion with the distributor in step 460 may subsequently confirm the informed consent. In other instances, the patient may decide not to obtain the medical therapy and line 472 leads to step 497, where the algorithm ends.

Step 480 delivers the substitute medical therapy to the patient. For example, the delivery may be by next day delivery with a return receipt and delivery only upon signature by the patient. In most instances, the distributor will facilitate access to the medical therapy and provide a means for verifying the delivery. The distributor may facilitate access to the substitute medical therapy by any one of several means. For example, the substitute medical therapy may be sent by mail or courier to the patient or physician or their representatives. If the substitute medical therapy is sent to the physician, the patient may pick it up from the physician's office, or the physician's office may mail or courier the drug to the patient. Alternatively, the substitute medical therapy may be sent by the manufacturer to a pharmacy where the patient might come by to pick it up in person. In another aspect, the pharmacy may also send the medical therapy by courier or by mail.

Step 485 determines whether the patient has received the substitute medical therapy. Receipt may be verified by a return receipt with a signature. Alternative means may be used to confirm receipt, for example, receipt by a receiving authority for the patient, including, but not limited to, the patient's physician or pharmacist. If the answer is "no" line 490, leads to step 465, where the distributor adds this information along with the previously received information and determines whether the patient still meets the requirements for access to the substitute medical therapy. At the distributor's discretion, in some situations, for example, the patient may be contacted to determine the reason for non-receipt and re-authorize the delivery of the substitute medical treatment. In other situations, additional diagnostic tests may be required (re-tests). In still other situations, the patient's physician or both the patient and patient's physician may be contacted for additional information.

If the answer step 485 is "yes", line 492 shows that step 495 is reached. Step 495 shows that the delivery of the substitute medical therapy to the patient will be confirmed and recorded. In step 495 the data recorded may include, for example, a copy of the patient's prescribing label, the patient's data and diagnostic tests and voice-recorded confirmation of informed consent provided in step 460, and the reasons for determining that the qualified patient was eligible for delivery of the substitute medical therapy by the distributor. If certain additional data is obtained verbally as part of a consultation, these discussions also may be voice-recorded and made part of this record. These records may be printed, displayed, transmitted to a location, such as a user terminal, other location designated by a user, or a memory coupled to the server, or processing device, executing certain aspects of algorithm 400. For example, the prescription data recorded in step 495 may be supplemented with additional prescribing data for this or other medical therapies by the distributor. In addition, the prescription data may be accessed by the distributor, manufacturer of the substitute medical therapy, or other regulatory body for quality control of the delivery process or for obtaining statistical or other data, as described in other embodiments of the present invention.

The algorithm ends, as shown in step 497.

The following examples describe scenarios to illustrate how the proposed method may be used for providing a substitute medical therapy to a patient.

EXAMPLE 1

Patient A is a 28 year old female and visits her physician B for a consult. Physician B, after consultation, concludes that Patient A could benefit from using the drug thalidomide. Physician B then consults Patient A, a woman of childbearing potential, and explains to her that thalidomide is a teratogen and causes severe birth defects if a fetus is exposed to the drug, and explains all the precautions that need to be taken before starting the therapy and during the therapy, including getting pregnancy testing. After the consultation, Physician B also asks the patient to watch the audiovisual program prepared by the current manufacturer, Company X. Patient A watches the audiovisual program and reads the written material provided by the Company X. A also signs an informed consent stating that her physician B has explained the program to her, that she has read, seen and understood the teratogenic dangers of the drug, and that she is willing and able to follow instructions relating to avoiding pregnancy while on the medication, and that she would comply with the program. Physician B then obtains a pregnancy test from Patient A, which confirms that Patient A is not currently pregnant. Physician B then writes a prescription for thalidomide. Patient A takes the prescription to her local pharmacy.

Pharmacist C at the pharmacy informs Patient A that there is an FDA approved generic pharmaceutical available from Company Y. Patient A determines that she would benefit from the generic substitute, e.g., it may cost substantially less with her medical insurance. Pharmacist C then sends the prescription via facsimile to Company Y. Company Y contacts Physician B and informs him that the patient has requested the generic substitute and requests copies of Patient A's relevant risk assessment documents, including the patient's medical history, including two previous negative pregnancy test results, her informed consent, and requests Physician B's certification that he will comply with the obligations of the risk management program for the generic substitute medical therapy.

Upon receipt of the documents, Company Y's health care personnel, preferably a physician or pharmacist or nurse, counsels Patient A to confirm she understands the risks, understands how to avoid pregnancy while on the medication, and knows what to do in case she is unable to comply with the program or suspects that she is pregnant while on the medication. In addition, Company Y also evaluates any potential drug-drug, drug-disease interactions that could compromise the treatment, harm the patient, or produce false positive or false negative pregnancy tests. Company Y may choose to voice-record the entire conversation. If Company Y believes that Patient A is an appropriate candidate for the thalidomide prescription, Company A then prepares to fill the prescription, makes the prescription label, affixes the label to the container or box with the medication, includes the patient guide and other relevant parts of the labeling as required, and delivers it to patient via a courier or by express mail. Once the courier service confirms that Patient A has received the medication, Company Y then records the prescription information and patient information, stores all the relevant risk assessment information, both electronically and physically in an easily retrievable format. Company Y sends a letter to Physician B that the prescription has been filled and the patient has received it. Company Y also includes a copy of the prescription label that has been attached to the medication box that is shipped to Patient A, and a copy of the courier confirmation of Patient A's receipt.

EXAMPLE 2

Example 2 is similar to Example 1 with respect to Patient A's diagnosis, treatment options, Physician B's activities and Patient A presenting the prescription to Pharmacist C. Pharmacist C then informs Patient A of the generic pharmaceutical option and Patient A agrees to have the prescription filled with the substitute. As in Example 1, Pharmacist C proceeds to fill the prescription, and chooses the generic pharmaceutical product from Company Y. The difference here is that the prescription then gets transmitted electronically to Company Y by using appropriate software on a secure network. Company Y retrieves the prescription information and contacts Physician B as described in Example 1. The rest of the procedure is the same as in Example 1.

EXAMPLE 3

Example 3 is analogous to Example 1 but for the following differences: the restricted distribution drug is lenalidomide; the risk-assessment relates to preventing exposure to a fetus.

EXAMPLE 4

Example 4 is analogous to Example 2 but for the following differences: the restricted distribution drug is lenalidomide; the risk-assessment relates to preventing exposure to a fetus.

EXAMPLE 5

Example 5 is analogous to Example 1 but for the following differences: the restricted distribution drug is isotretinoin; the risk-assessment relates to preventing exposure to a fetus.

EXAMPLE 6

Example 6 is analogous to Example 2 but for the following differences: the restricted distribution drug is isotretinoin; the risk-assessment relates to preventing exposure to a fetus.

EXAMPLE 7

Example 7 is analogous to Example 1 but for the following differences: the restricted distribution drug is bosentan; the risk-assessment relates to assessing pregnancy and liver function.

EXAMPLE 8

Example 8 is analogous to Example 2 but for the following differences: the restricted distribution drug is bosentan; the risk-assessment relates to assessing pregnancy and liver function.

EXAMPLE 9

Example 9 is analogous to Example 1 but for the following differences: the restricted distribution drug is alosetron; the risk-assessment relates to preventing life-threatening ischemic colitis.

EXAMPLE 10

Example 10 is analogous to Example 2 but for the following differences: the restricted distribution drug is alosetron; the risk-assessment relates to preventing life-threatening ischemic colitis.

EXAMPLE 11

Example 11 is analogous to Example 1 but for the following differences: the restricted distribution drug is dofetilide; the risk-assessment relates to preventing drug-drug interactions or drug-disease interactions that may induce life-threatening ventricular arrhythmia.

EXAMPLE 12

Example 12 is analogous to Example 2 but for the following differences: the restricted distribution drug is dofetilide; the risk-assessment relates to preventing drug-drug interactions or drug-disease interactions that may induce life-threatening ventricular arrhythmia.

EXAMPLE 13

Example 13 is analogous to Example 1 but for the following differences: the restricted distribution medical therapy is a product with the potential for substance abuse or chemical dependence, such as oxycodone, marijuana, and cannabis, and the risk assessment involves reducing the risk for such abuse.

EXAMPLE 14

Example 14 is analogous to Example 2 but for the following differences: the restricted distribution medical therapy is a product with the potential for substance abuse or chemical dependence, such as oxycodone, marijuana, and cannabis, and the risk assessment involves reducing the risk for such abuse.

EXAMPLE 15

Example 15 is analogous to Example 1 but for the following differences: the restricted distribution medical therapy, such as clozapine or any of the preceding drugs, requires ongoing diagnostic testing for continued therapy.

EXAMPLE 16

Example 16 is analogous to Example 2 but for the following differences: the restricted distribution medical therapy, such as clozapine or any of the preceding drugs, requires ongoing diagnostic testing for continued therapy.

Thus, while fundamental novel features of the invention shown and described and pointed out, it will be understood that various omissions and substitutions and changes in the form and details of the devices illustrated, and in their operation, may be made by those skilled in the art without departing from the spirit of the invention. For example, it is expressly intended that all combinations of those elements and/or method steps which perform substantially the same function in substantially the same way to achieve the same results are within the scope of the invention. Moreover, it should be recognized that structures or elements or method steps shown or described in connection with any disclosed form or embodiment of the invention may be incorporated in another form or embodiment. It is the intention, therefore, to be limited only as indicated by the scope of the claims appended hereto.

The invention claimed is:

1. A method for providing restricted access to a generic drug that has been approved by the Food and Drug Administration (FDA) as substitutable for a branded restricted distribution drug to a patient to whom the branded restricted distribution drug was prescribed by a physician, wherein the branded restricted distribution drug is a drug that requires compliance with an FDA-approved risk management program comprising a generic drug manufacturer:

authorizing fulfillment of the generic drug to the patient only after determining the patient's eligibility has been determined in accordance with an FDA-approved risk management program for the generic drug and, if necessary, after approval is obtained from a prescribing physician to substitute the generic drug for the branded restricted distribution drug, wherein the fulfillment is provided by one of: a pharmacy, the prescribing physician, the generic drug manufacturer, or a distributor, or a combination thereof; and wherein the distribution of the generic drug is not authorized if the patient is determined to be ineligible;

provided that authorizing the fulfillment of the generic drug to the patient does not comprise the generic drug manufacturer or distributor:

generating a validation code to dispense the generic drug prior to fulfillment of the prescription; or requiring the patient, the pharmacy, or the prescribing physician to be registered with the generic drug manufacturer or distributor prior to the fulfillment of the prescription; and wherein, after authorizing the fulfillment of the generic drug to the patient, data about the eligibility determination of patient for the generic drug, the physician information, the patient information, and the generic drug delivered are recorded in a computer-readable medium.

2. The method of claim 1, wherein the generic drug is a product with the potential for substance abuse or chemical dependence.

3. The method of claim 1, wherein the generic drug requires ongoing diagnostic testing for continued therapy.

4. The method of claim 1, wherein the generic drug is thalidomide.

5. The method of claim 1, wherein the generic drug is lenalidomide.

6. The method of claim 1, wherein the generic drug is isotretinoin.

7. The method of claim 1, wherein the generic drug is bosentan.

8. The method of claim 1, wherein the generic drug is alosetron.

9. The method of claim 1, wherein the generic drug is dofetilide.

10. The method of claim 1, wherein the generic drug is oxycodone.

11. The method of claim 1, wherein the generic drug is cannabis.

12. The method of claim 1, wherein the generic drug is clozapine.

13. A method for providing restricted access to a generic drug that has been approved by FDA as substitutable for a branded restricted distribution drug to a patient to whom the branded restricted distribution drug was prescribed by a physician, wherein the branded restricted distribution drug is a drug that requires compliance with an FDA-approved risk management program comprising a generic drug manufacturer or distributor:

providing a generic drug for a branded drug that is designated as a restricted distribution drug;

receiving a request for distribution of the generic drug for a specific patient;

obtaining relevant risk-assessment documents from the prescriber who originated the request for the patient;

evaluating the documents for eligibility of the patient for the generic drug under the restricted access program of the generic drug and the prescription for the branded drug;

authorizing fulfillment of the generic drug to the patient only after determining the patient's eligibility has been determined in accordance with an FDA-approved risk management program for the generic drug and, if necessary, after approval is obtained from a prescribing physician to substitute the generic drug for the branded restricted distribution drug, wherein the fulfillment is provided by one of: a pharmacy, the prescribing physician, the generic drug manufacturer, or a distributor, or a combination thereof; and wherein the distribution of the generic drug is not authorized if the patient is determined to be ineligible;

provided that authorizing the fulfillment of the generic drug to the patient does not comprise the generic drug manufacturer or distributor:

generating a validation code to dispense the generic drug prior to fulfillment of the prescription; or requiring the patient, the pharmacy, or the prescribing physician to be registered with the generic drug manufacturer or distributor prior to the fulfillment of the prescription; and wherein, after authorizing the fulfillment of the generic drug to the patient, data about the eligibility determination of the patient for the generic drug, the physician information, the patient information, and the generic drug delivered are recorded in a computer-readable medium.

14. The method of claim 13, wherein the generic drug is a product with the potential for substance abuse or chemical dependence.

15. The method of claim 13, wherein the generic drug requires ongoing diagnostic testing for continued therapy.

16. The method of claim 13, wherein the generic drug is thalidomide.

17. The method of claim 13, wherein the generic drug is lenalidomide.

18. The method of claim 13, wherein the generic drug is isotretinoin.

19. The method of claim 13, wherein the generic drug is bosentan.

20. The method of claim 13, wherein the generic drug is alosetron.

21. The method of claim 13, wherein the generic drug is dofetilide.

22. The method of claim 13, wherein the generic drug is oxycodone.

23. The method of claim 13, wherein the generic drug is cannabis.

24. The method of claim 13, wherein the generic drug is clozapine.

25. A method for delivering a substitute medical therapy product that has been approved by the FDA as substitutable for a branded restricted distribution medical therapy to a patient to whom the branded restricted distribution medical therapy was prescribed by a physician, wherein the branded restricted distribution medical therapy is a medical therapy that requires compliance with an FDA-approved risk management program comprising a substitute medical therapy manufacturer or distributor:

describing features to obtain the substitute medical therapy for a qualifying patient for whom the branded medical therapy is prescribed;

obtaining data and informed consent from the patient to receive the substitute medical therapy for the branded medical therapy, wherein the consent includes an authorization to release the patient's medical records to deliver the substitute medical therapy;

authorizing fulfillment of the substitute medical therapy to the patient only after determining the patient's eligibility has been determined in accordance with an FDA-approved risk management program for the substitute medical therapy and, if necessary, after approval is obtained from a prescribing physician to substitute the medical therapy for the branded restricted distribution medical therapy, wherein the fulfillment is provided by one of: a pharmacy, the prescribing physician, the substitute medical therapy manufacturer, or a distributor, or a combination thereof; and wherein the distribution of the medical therapy is not authorized if the patient is determined to be ineligible;

provided that authorizing the fulfillment of the substitute medical therapy does not comprise the substitute medical therapy manufacturer or distributor:

generating a validation code to dispense the substitute medical therapy prior to fulfillment of the prescription; or requiring the patient, the pharmacy, or the prescribing physician to be registered with the substitute medical therapy manufacturer or distributor prior to fulfillment of the prescription; and providing, to a distributor of the substitute medical therapy, the authorization, certification data, and informed consent from the qualified patient, and required diagnostic tests, wherein the certification data includes conclusions from the prescribing physician that the patient is a qualified patient for the substitute medical therapy and representations that the prescribing physician will follow the requirements of the restricted access program for the substitute medical therapy;

confirming the informed consent from the qualified patient to the distributor of the substitute medical therapy;

wherein, after authorizing the fulfillment of the substitute medical therapy to the patient, data about the eligibility determination of the patient for the substitute medical therapy, the physician information, the patient information, and the substitute medical therapy delivered are recorded in a computer-readable medium.

26. The method of claim 25, further comprising:
obtaining data regarding a procedure for delivering a substitute medical therapy.

27. The method of claim 25, further comprising:
confirming and recording in a computer-readable medium prescription data including the prescription label.

28. The method of claim 25, further comprising:
obtaining additional data from the qualified patient to determine present or future qualification or eligibility for the substitute medical therapy.

29. The method of claim 25, wherein the substitute medical therapy is a product with the potential for substance abuse or chemical dependence.

30. The method of claim 25, wherein the substitute medical therapy requires ongoing diagnostic testing for continued therapy.

31. The method of claim 25, wherein the substitute medical therapy is thalidomide.

32. The method of claim 25, wherein the substitute medical therapy is lenalidomide.

33. The method of claim 25, wherein the substitute medical therapy is isotretinoin.

34. The method of cl aim 25, wherein the substitute medical therapy is bosentan.

35. The method of claim 25, wherein the substitute medical therapy is alosetron.

36. The method of claim 25, wherein the substitute medical therapy is dofetilide.

37. The method of claim 25, wherein the substitute medical therapy is oxycodone.

38. The method of claim 25, wherein the substitute medical therapy is cannabis.

39. The method of claim 25, wherein the substitute medical therapy is clozapine.

40. The method of claim 25, further comprising:
obtaining additional data from the qualified patient for quality control.

* * * * *

UNITED STATES PATENT AND TRADEMARK OFFICE
CERTIFICATE OF CORRECTION

PATENT NO. : 7,885,827 B1  
APPLICATION NO. : 12/813028  
DATED : February 8, 2011  
INVENTOR(S) : Phanesh Koneru Page 1 of 1

It is certified that error appears in the above-identified patent and that said Letters Patent is hereby corrected as shown below:

On the Title page

Item 73, Amend assignee from
"Exela Pharmsci, Inc." to --Exela PharmSci, Inc.--.

Signed and Sealed this
Nineteenth Day of April, 2011

David J. Kappos
*Director of the United States Patent and Trademark Office*